(12) United States Patent
Khachaturov et al.

(10) Patent No.: US 11,419,679 B2
(45) Date of Patent: Aug. 23, 2022

(54) OPTIMIZATION OF BPH TREATMENT USING LEP (LASER ENUCLEATION OF PROSTATE)

(71) Applicant: LUMENIS LTD., Yokneam (IL)

(72) Inventors: Arkady Khachaturov, Haifa (IL); Tal Waisman, Haifa (IL); Eyal Benisty, Kfar Hachoresh (IL); Mikhael Feldchtein, Kiryat Yam (IL)

(73) Assignee: Lumenis Ltd., Yokneam (IL)

( * ) Notice: Subject to any disclaimer, the term of this patent is extended or adjusted under 35 U.S.C. 154(b) by 381 days.

(21) Appl. No.: 16/367,748

(22) Filed: Mar. 28, 2019

(65) Prior Publication Data

US 2019/0298449 A1    Oct. 3, 2019

Related U.S. Application Data

(63) Continuation-in-part of application No. 16/177,800, filed on Nov. 1, 2018, now Pat. No. 10,799,291.
(Continued)

(51) Int. Cl.
*A61B 18/22* (2006.01)
*A61N 5/06* (2006.01)
*A61B 18/00* (2006.01)

(52) U.S. Cl.
CPC .............. *A61B 18/22* (2013.01); *A61N 5/062* (2013.01); *A61N 5/0603* (2013.01);
(Continued)

(58) Field of Classification Search
CPC combination set(s) only.
See application file for complete search history.

(56) References Cited

U.S. PATENT DOCUMENTS 5,321,715 A   6/1994 Trost
5,409,479 A   4/1995 Dew et al.
(Continued)

FOREIGN PATENT DOCUMENTS

CN   1282230 A   1/2001
CN   1839771 A   10/2006
(Continued)

OTHER PUBLICATIONS

Search Report—Corresponding PCT Application No. PCT/IL2019/050362, filed Mar. 28, 2019, 4 pages.
(Continued)

*Primary Examiner* — Scott Luan
(74) *Attorney, Agent, or Firm* — Seager, Tufte & Wickhem, LLP

(57) ABSTRACT

Apparatus for the treatment of a target tissue with a laser beam in which the target tissue is immersed in a liquid medium within a body lumen. The laser device is configured to provide one or more laser pulses which are configured by a controller to have an energy sufficient to form one or more vapor bubbles in the liquid medium at the distal delivery end of the fiber. The one or more pulses are configured by the controller to: first, cause a vapor bubble to be formed distally of the distal end portion of the endoscope and around the distal delivery end of the optical fiber; second, cause a second bubble to be formed distally of the first bubble; and, third, inflate the second bubble as the first bubble has begun to collapse to expand an amount sufficient to displace a substantial portion of the liquid medium from the space between the distal delivery end of the fiber and the target tissue.

14 Claims, 6 Drawing Sheets

Related U.S. Application Data

(60) Provisional application No. 62/649,930, filed on Mar. 29, 2018.

(52) U.S. Cl.
CPC ............ *A61B 2018/00547* (2013.01); *A61B 2018/00577* (2013.01); *A61B 2018/2205* (2013.01); *A61B 2018/2255* (2013.01); *A61N 2005/061* (2013.01)

(56) References Cited

U.S. PATENT DOCUMENTS

| | | | |
|---|---|---|---|
| 5,632,739 A * | 5/1997 | Anderson | A61B 18/24 606/15 |
| 9,017,316 B2 | 4/2015 | Khatchaturov et al. | |
| 10,524,821 B2 | 1/2020 | Preiss et al. | |
| 2009/0126235 A1 | 5/2009 | Kobayashi et al. | |
| 2013/0084544 A1 | 4/2013 | Boutoussov et al. | |
| 2014/0336626 A1 | 11/2014 | Jiang et al. | |
| 2015/0223911 A1 | 8/2015 | Lukac et al. | |
| 2016/0015471 A1 | 1/2016 | Piron et al. | |
| 2017/0036253 A1* | 2/2017 | Lukac | B08B 7/02 |

FOREIGN PATENT DOCUMENTS

| | | |
|---|---|---|
| CN | 102264434 A | 11/2011 |
| CN | 102389333 A | 3/2012 |
| CN | 104302347 A | 1/2015 |
| CN | 105764436 A | 7/2016 |
| EP | 2939631 A1 | 11/2015 |
| WO | 9920189 A1 | 4/1999 |
| WO | 2017212404 | 12/2017 |

OTHER PUBLICATIONS

Search Report—Corresponding PCT Application No. PCT/IB17/053333, dated Sep. 19, 2017, 5 pages.
Search Report—European Application No. 17809815.8 dated Jan. 22, 2020, 8 pages.
Van Leeuwen, TG., et al., "Noncontact tissue ablation by Holmium:YSGG laser pulses in blood," Lasers in Surgery and Medicine, 11(1):26-34 (1991) Abstract.
Extended European Search Report for EP Application No. 19774625.8, dated Nov. 23, 2021, 10 pages.
Hutchens, T.C., et al, "Fiber optic muzzle brake tip for reducing fiber burnback and stone retropulsion during thulium fiber laser lithotripsy" Journal of Biomedical Optics 22(1): 18001 (2017).

* cited by examiner

OPTIMIZATION OF BPH TREATMENT USING LEP (LASER ENUCLEATION OF PROSTATE)

RELATED APPLICATIONS

This application is related to and claims priority to U.S. Provisional Application Ser. No. 62/649,930, filed Mar. 29, 2018, the entire contents of which are herein incorporated by reference. This application is also related to, claims priority to, and is a continuation in part of pending U.S. patent application Ser. No. 16/177,800, filed Nov. 1, 2018. The entire contents of both applications are herein incorporated by reference.

FIELD OF THE INVENTION

The present invention is directed to laser devices useful in the treatment of benign prostate hyperplasia (BPH), and in particular devices useful, for example, in performing laser enucleation of the prostate (LEP), which, when performed using a Holmium laser device is abbreviated as HoLEP and when performed using a Thulium laser device is abbreviated as ThuLEP. The present invention may also be useful in performing laser ablation of the prostate (LAP), which, when performed using a Holmium laser is known as HoLAP.

This invention relates to laser light energy sources and to methods and devices for reducing the attenuation of a laser beam which will transit through a liquid environment to a target tissue in laser lithotripsy, reduction of optical fiber burnback and target tissue retropulsion, LEP and other relevant fields where a laser is used in a liquid environment.

BACKGROUND OF THE PRESENT INVENTION

Benign Prostatic Hyperplasia (BPH) has been treated successfully using a well-known laser enucleation procedure, a procedure (known is the industry as "LEP") in which the grown prostate tissue (prostatic adenoma) is separated from its surrounding prostatic capsule and other organs such as seminal colliculus and other landmarks, by cutting into the prostate without harming the capsule itself. The separated tissue, usually cut into a number of pieces, is then pushed into the bladder. The pieces may then be morcellated using a mechanical morcellation device to grind up the pieces to a size in which they can be removed from the body. A device such as that described in pending U.S. patent application Ser. No. 15/710,316, filed Sep. 20, 2017 and entitled "System and Method for Morcellation of Tissue" (which application is herein incorporated by reference in its entirety) may be suitable for performing this tissue removal task. In addition, laser-based morcellation devices may be employed. The entire procedure is performed, using endoscopic techniques through natural body orifices.

The LEP procedure has been found to be very beneficial for the patient because it has generally a very low reoperation rate due to the fact that there is no prostate regrowth because all of the prostate tissue is removed, unlike other types of procedures (like TURP). Due to the very low complication rate, the patient's recovery is quicker and less painful than some other procedures.

In the first step of a typical LEP procedure, an incision may be made through the prostate tissue to reach the capsule. This is usually done at predetermined positions to help the surgeon's orientation, e.g., at "1 o'clock", "11 o'clock" positions. Some physicians are practicing different cuts such as "5 o'clock" and "7 o'clock", "12 o'clock" or others. After the prostate-capsule border is reached, the surgeon may fire the laser along the anatomical boundaries of the prostate gland material and the capsule, thus creating a separating plane between the two.

During a LEP procedure, an optical fiber is inserted through a working channel of a ureteroscope as well as irrigation and visualization systems. The working environment of a laser radiation emitted from a tip of the optical fiber toward a target tissue, is therefore a liquid environment. Liquid environment tends to absorb optical energy and therefore may affect both, the adjacent liquid environment itself as well as the characteristics of the emitted laser beam as it reaches a target tissue. As mentioned in the aforementioned U.S. patent application Ser. No. 16/177,800, and in its incorporated references, a great deal of attention is given to the interaction of the laser beam with the surrounding liquid within the working environment as well as how to increase the efficacy of the optical energy in lithotripsy and the reduction of stone retropulsion.

More specifically, some aspects of the incorporated references disclose the creation and control of vapor bubbles during lithotripsy within the liquid working environment due to its optical energy absorbance characteristics. The MOSES™ effect is described and optimized in these documents, where a controlled amount of energy creates a vapor bubble to vaporize the liquid in the environment, and then the remaining energy is delivered through the vapor bubble toward a targeted stone. It is one aspect of the present invention to use and optimize this laser-liquid interaction during a LEP procedure, by controlling different laser and beam characteristics, in order to create bubbles that improve the mechanical tissue separation.

When the laser is fired, it may create a vapor bubble in front of the fiber tip, the bubble being caused by the laser vaporizing the liquid material present at the site, as described in the aforementioned U.S. patent application Ser. No. 16/177,800. In the lithotripsy procedure described in the aforesaid U.S. patent application Ser. No. 16/177,800, one or more vapor bubbles created by the laser device are used to create a "pathway" to, in such procedures, break up or disintegrate, for example, kidney stones or other abnormal growths that may be present and "floating around" the urinary tract, the kidneys or the bladder. By vaporizing the liquid material between the object to be targeted and a laser fiber tip which carries laser energy from, for example, the Holmium laser or a Thulium laser or an Erbium laser, to the targeted stone, a more efficient treatment may result due to the absence of liquid in the "pathway". According to an aspect of the present invention, a surgeon may be able to create one or more bubbles with the laser in the liquid working environment during a LEP procedure and employ the vapor bubble created by the laser pulse to mechanically cut the prostate or separate it from its capsule or other organs. Also, the one or more bubbles' path to the target tissue may allow for easier visual tracking of the laser cutting plane.

In a LEP procedure, three terms may be associated with this surgical procedure: 1. the above mentioned and incorporated art related to the MOSES™ effect and its optimization; 2. a photo-mechanical effect—in which the laser energy creates a vapor bubble, which, as discussed above in a LEP procedure and in accordance to the present invention is being used to mechanically separate the tissue during its inflation or by its cavitation during its collapse (as opposed to the MOSES™ photo-mechanical effect in lithotripsy on a target tissue); and, 3. a photo-thermal effect—in which laser energy is delivered directly to the tissue, causing thermal damage, thus creating an incision, or an ablative or coagulative effect (again, as opposed to the MOSES™ photothermal effect in lithotripsy on a target tissue).

In present day lithotripsy procedures, a typical equipment setup is illustrated in FIG. 1. The equipment 100 includes an optical laser fiber or a light guide 102 connected at its proximal end 104 to a laser source 106, which may be a laser source such as Holmium, Thulium, Erbium or others. The laser fiber or the light guide 102 is passed through an endoscope 108 and its distal end or tip 110 extends out from the distal end 112 of the endoscope. Regular mode pulses fire a continuous amount of energy from the fiber distal end 110 into the liquid environment surrounding the fiber, and between the fiber and the target tissue 114. This firing causes the inflation of a growing bubble followed by its collapse, typically a symmetrical bubble 116 is inflated, with its center positioned about the fiber tip 110.

One problem associated with this prior art setup of FIG. 1 is the negative effects that the bubble(s) may cause both to the fiber tip and to the distal end of the endoscope. The vapor bubble 116, as seen in FIG. 1, expands not only toward the target tissue but backwards as well and this bubble with its contained energy may impact the distal end of the endoscope, and during its collapse may impact the fiber or even the ureteroscope itself, thus creating fiber so-called "burnback" or degradation of the fiber. Fiber burnback is a known condition that may cause the fiber tip to degrade to such an extent so as to impede or at least make less efficient the treatment parameters. Further, the backward development of the bubble represents optical energy loss which was absorbed by the liquid but has not improved the MOSES™ effect and therefore lessens the efficiency of the tissue treatment by reducing the energy available to impact the treatment of the target tissue such as, for example, prostate or urinary tract stone.

Thus, it would be desirable to provide an apparatus and method in which fiber burnback is eliminated or lessened, with the concomitant effects of reducing wear on the endoscope as well as providing more optical energy delivered to the target tissue and enhance ablation and coagulation by utilizing the MOSES™ effect, creating and controlling bubbles to enhance tissue separation. It is to this goal that the present invention is directed, at least in part.

Further, in the aforesaid U.S. patent application Ser. No. 16/177,800, there is described therein, in relation to FIG. 3B, a step 400 in which the user may select a "pair of pulses" repetition rate. The specification further describes this step 400 as the repetition rate between pairs of pulses, one of which may be a bubble initiation pulse and the second a treatment pulse. It has been found that by manipulating the timing of the pairs of pulses that better treatment parameters may be had. It is further to this goal that the present invention is also directed.

Also, the aforesaid U.S. patent application Ser. No. 16/177,800 describes a fiber tip in general but does not provide any further mechanisms to control bubble formation and shape. It is the mechanisms to control bubble formation and shapes that the present invention is also directed.

SUMMARY OF THE PRESENT INVENTION

In an aspect, a method of treating a target tissue with a laser beam, the target tissue being immersed in a liquid medium within a body lumen, the method includes: providing a laser device for generating a laser beam; providing an endoscope configured to be introduced into the body lumen, the endoscope having a distal end portion; providing an optical fiber or a light guide configured to be contained in the endoscope and having a distal delivery end for guiding the laser beam to the target tissue, wherein the distal delivery end protrudes a distance from the distal end portion of the endoscope; and providing a controller for causing the laser device to generate one or more laser pulses substantially along the same longitudinal axis. In LAP procedures (laser ablation of the prostate) a side firing fiber or wave guide may be used. The controller causes the laser device to provide one or more laser pulses, the one or more laser pulses being configured by the controller to have an energy sufficient to form one or more vapor bubbles in the liquid medium at the distal delivery end of the fiber; the one or more pulses are configured by the controller to: first, causing a vapor bubble to be formed distally of the distal end portion of the endoscope and around the distal delivery end of the optical fiber or a light guide; second, causing a second vapor bubble to be formed distally of the first bubble, the second vapor bubble being distal of both the endoscope distal end portion and the optical fiber distal delivery end; and third, inflating the second bubble as the first bubble has begun to collapse to expand an amount sufficient to displace a substantial portion of the liquid medium from the space between the distal delivery end of the fiber and the target tissue, the one or more pulses being delivered to the target tissue through the inflated second bubble; the displacement of the second bubble away from the distal portion of the endoscope and the distal delivery end of the optical fiber reduces wear and/or injury to one or more of the endoscope and the optical fiber.

In another aspect, an apparatus for the treatment of a target tissue with a laser beam, in which the target tissue is immersed in a liquid medium within a body lumen, includes: a laser device for generating a laser beam; an endoscope configured to be introduced into the body lumen, the endoscope having a distal end portion; an optical fiber or light guide configured to be contained in the endoscope and having a distal delivery end for guiding the laser beam to the target tissue, wherein the distal delivery end protrudes a distance from the distal end portion of the endoscope; a controller for causing the laser device to generate one or more laser pulses substantially along or aside the same longitudinal axis. The laser device is configured to provide one or more laser pulses, the one or more laser pulses being configured by the controller to have an energy sufficient to form one or more vapor bubbles in the liquid medium at the distal delivery end of the fiber. The one or more pulses are configured by the controller to: first, cause a vapor bubble to be formed distally of the distal end portion of the endoscope and around the distal delivery end of the optical fiber or a light guide; second, cause a second vapor bubble to be formed distally of the first bubble, the second vapor bubble being distal of both the endoscope distal end portion and the optical fiber distal delivery end; third, inflate the second bubble as the first bubble has begun to collapse to expand an amount sufficient to displace a substantial portion of the liquid medium from the space between the distal delivery end of the fiber and the target tissue, the one or more pulses being delivered to the target tissue through the inflated second bubble. The displacement of the second bubble away from the distal portion of the endoscope and the distal delivery end of the optical fiber reduces wear and/or injury to one or more of the endoscopes and the optical fiber.

In a further aspect, the one or more laser pulses is more than one train of pulses, and the method further comprising the step of the controller of selecting a repetition rate for delivery of the more than one laser pulses. The method also may include selecting at least one of the following parameters through the controller: selecting the total energy of one or more pulses to be delivered to the target tissue, selecting the pulse length of one or more pulses to be delivered to the target tissue, selecting the pulse energy, selecting the time delay between successive train of one or more pulses, selecting the laser (wavelength) to be used for a one or more pulses, selecting the fiber size, selecting the required clinical result and selecting the distance from the delivery end to the target tissue.

In yet another aspect, the method may further include the steps of: measuring actual energy irradiated by the laser device; comparing the actual measured energy to a total energy selected by the controller; and, if the comparison demonstrates variance of the actual measured energy from the selected total energy, the controller adjusting the energy or pulse length for any following pulses to achieve the selected energy delivered to the target tissue. The target tissue may be a tissue, an organ or a formed stone within a human body.

In an aspect, the method may also include the step of selecting and mounting on the laser device an optical fiber or a light guide type to be used in irradiating the target tissue. The type of optical fiber or wave guide includes at least one of the parameters of: fiber diameter, fiber material, fiber numerical aperture and shape of the distal delivery end. The step of selecting the distance from the delivery end to the target tissue may include the further step of measuring the distance and selecting the measured distance. The step of measuring the actual energy delivered by the laser is performed by a photodetector in the light path of the laser radiation or in the light path of back scattered laser light from a target tissue.

In another aspect, the step of the controller adjusting the energy is accomplished by a closed loop feedback circuit operatively connected to the controller. The controller may intermittently recognize parameters associated with the fiber type mounted on the laser device. The step of automatically recognizing is performed by a RFID identification tag mounted on the delivery device and on the waveguide or optical fiber. The controller may indicate on a user interface associated with the controller if the optical fiber type is compatible with a treatment selected.

In an aspect, a method of treating a target tissue with a laser beam, in which the target tissue is immersed in a liquid medium within a body lumen or in which the laser beam has to cross a liquid medium on its way to a target tissue, includes:

providing a laser device for generating a laser beam; providing an optical fiber or a light guide having a distal delivery end for guiding the laser beam to the target tissue; providing a controller for causing the laser device to generate one or more laser pulses substantially along or lateral to the same longitudinal axis; the controller causing the laser device to provide a plurality of laser pulses, the plurality of laser pulses being configured by the controller to have an energy sufficient to form one or more vapor bubbles in the liquid medium at the distal delivery end of the fiber; the plurality of laser pulses may be selected by the controller to allow the one or more vapor bubbles to expand an amount sufficient to displace a substantial portion of the liquid medium from the space between the delivery end of the fiber and the target tissue, the plurality of pulses being delivered to the target tissue through the one or more vapor bubbles, wherein time intervals between adjacent pulses of the plurality of pulses are non-uniform. The treatment may be prostate enucleation, and one or more pulses may be first configured for mechanical tissue separation, followed by one or more pulses configured to incise the mechanically separated tissue. On the other hand, the treatment may be stone lithotripsy to diminish kidney stones, and wherein one or more pulses are first configured to cause cavitation to bring stones in front of the laser fiber, followed by a series of low energy, high repetition rate pulses to effect stone dusting to diminish kidney stones. Further, the treatment may be prostate enucleation or vaporization, and one or more pulses may be first configured to one or more of incising or ablating the target tissue, followed by one or more pulses configured to coagulate the tissue one or more of incised or ablated.

In yet a further aspect, an apparatus for treating a target tissue with a laser beam, in which the target tissue may be immersed in a liquid medium within a body lumen or in which the laser beam has to cross a liquid medium on its way to a target tissue, includes: a laser device for generating a laser beam; an optical fiber or a light guide having a distal delivery end for guiding the laser beam to the target tissue; a controller configured to cause the laser device to generate one or more laser pulses substantially along the same longitudinal axis or laterally; the controller is further configured to cause the laser device to provide a plurality of laser pulses, the plurality of laser pulses being configured by the controller to have an energy sufficient to form one or more vapor bubbles in the liquid medium at the distal delivery end of the fiber; the plurality of laser pulses may be configured by the controller to allow the one or more vapor bubbles to expand an amount sufficient to displace a substantial portion of the liquid medium from the space between the delivery end of the fiber and the target tissue, the plurality of pulses being delivered to the target tissue through the one or more vapor bubbles, wherein time intervals between adjacent pulses of the plurality of pulses are non-uniform.

In another aspect, the treatment may be prostate enucleation, and wherein one or more pulses are first configured for mechanical tissue separation, followed by one or more pulses configured to incise the mechanically separated tissue. In addition, the treatment may be stone lithotripsy to diminish kidney stones, and wherein one or more pulses are first configured to cause cavitation to bring stones in front of the laser fiber or the light guide, followed by a series of low energy, high repetition rate pulses to effect stone dusting to diminish kidney stones. Also, the treatment may be prostate enucleation or vaporization, and wherein one or more pulses are first configured to one or more of incising or ablating the target tissue, followed by one or more pulses configured to coagulate the tissue one or more of incised or ablated.

In yet a further aspect, apparatus for the treatment of a target tissue with a laser beam, in which the target tissue being immersed in a liquid medium within a body lumen or in which the laser beam has to cross a liquid medium on its way to a target tissue, includes: a laser device for generating a laser beam; an endoscope configured to be introduced into the body lumen, the endoscope having a distal end portion; an optical fiber configured to be contained in the endoscope and having a distal delivery end for guiding the laser beam to the target tissue, wherein the distal delivery end protrudes a distance from the distal end portion of the endoscope. A tubular hollow choke may be configured to be mounted onto one of: the distal delivery end of the optical fiber or light guide or the distal end portion of the endoscope; the choke may be configured, when the laser device generates a laser beam, to shape a vapor bubble formed distally of one of: the distal end portion of the endoscope or the distal end of the optical fiber or light guide. The tubular hollow choke may be one of: cylindrical or tapering frustoconical shape. Further, the tapering may be either tapered to increase or decrease from a proximal end to a distal end of the frustoconical shaped hollow choke.

DETAILED DESCRIPTION OF THE PRESENT INVENTION

Bubble Manipulation to Reduce Fiber Tip Burnback and Endoscope Damage

As described above, it may be desirable to be able to manipulate the bubble formation caused by the firing of the laser device to cause a "shift" of the bubble(s) formed "forward" (or otherwise away from the fiber tip) to a distance in front of the fiber to reduce burnback, to reduce endo scope wear and to make more efficient use of photo-mechanical effects as described above. One of the techniques disclosed in the aforementioned patent application is known in the industry as the MOSES™ technology and comprises generally generating two or more bubbles, the first of which may vaporize the fluid present and the second of which may provide treatment to the target tissue. However, it is to be understood that the description just provided is not in any way a limiting disclosure and is no substitute for a thorough review and understanding of the aforementioned patent application.

Figure 1:
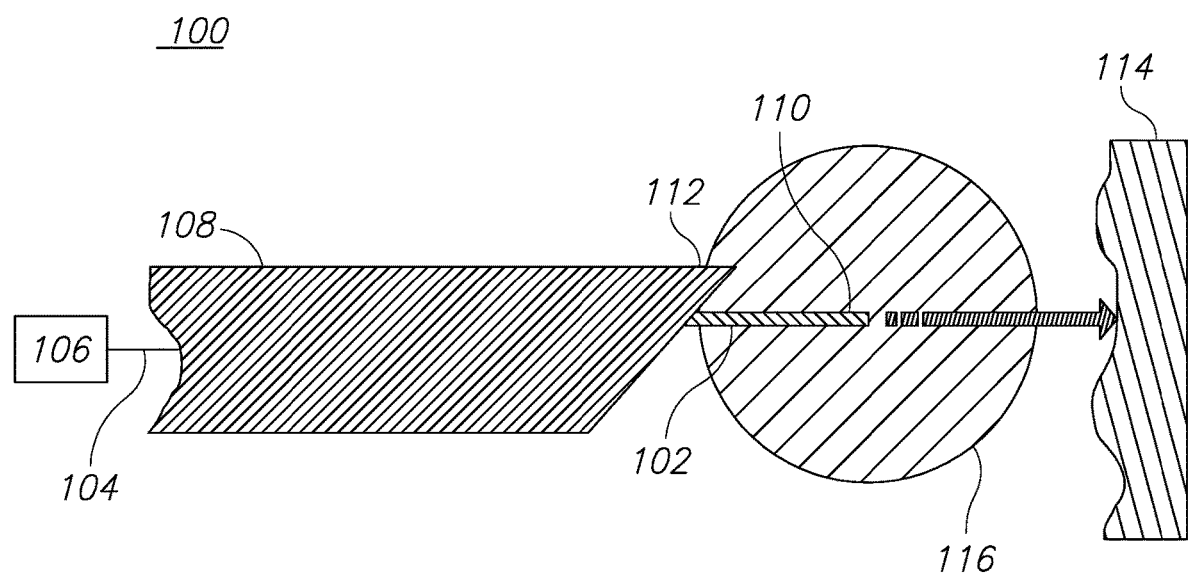
FIG. 1 illustrates a representation of a prior art device.
Figure 2:
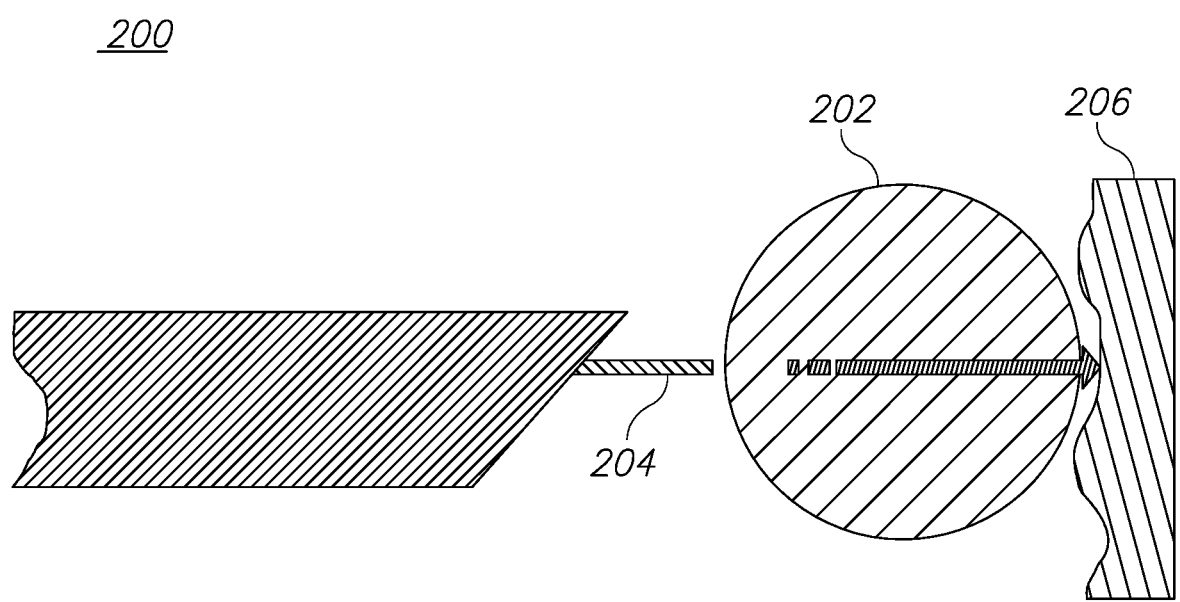
FIG. 2 illustrates an aspect of bubble formation of the present invention.

Turning now to FIG. 2, this figure illustrates one embodiment of the present invention in which a vapor bubble has been moved distally from a position in which it impinges on both the fiber tip and the endoscope, as in FIG. 1, to a position shown in FIG. 2 in which the bubble 202 has been distanced from the endoscope 200 tip and the fiber tip 204 and closer to the target tissue 206.

In this way, the bubble 202 is positioned to be formed further away distally from both the endoscope and the fiber. As mentioned above in relation to FIG. 1, a bubble tends to be developed around the tip of a fiber at its center. Since a bubble created by the laser also tends to collapse to its center through cavitation, it may damage the tip of the fiber or the adjacent tip of the scope. The larger the bubble, the larger the potential of damaging. The advantage of moving a bubble formation location distally is that when the bubble collapses it is not collapsed on the tip of the fiber or scope and may cause stronger photo-mechanical effects on a target tissue. Another advantage is that the bubble does not impact the endoscope 200 or cause burnback of the fiber tip 204, thus reducing the possibility of damage and wear-and-tear. Also, as the bubble collapses towards its center, which is located away from the fiber tip, this reduces fiber tip burnback and degradation due to the bubble collapse shockwaves.

Figure 3A:
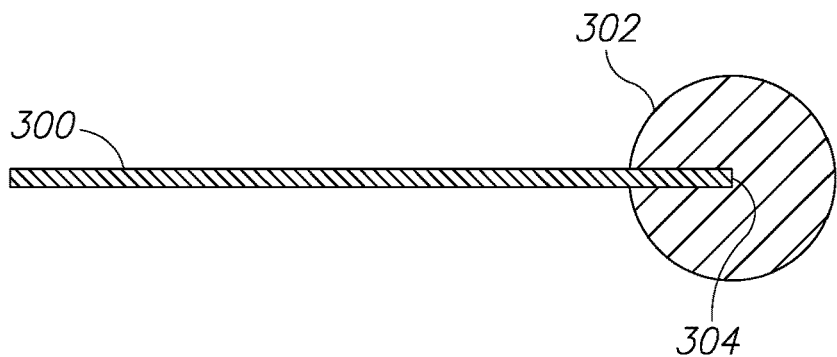
FIGS. 3A through 3C illustrate a sequence of the formation of bubbles in connection with the present invention.
Figure 3B:
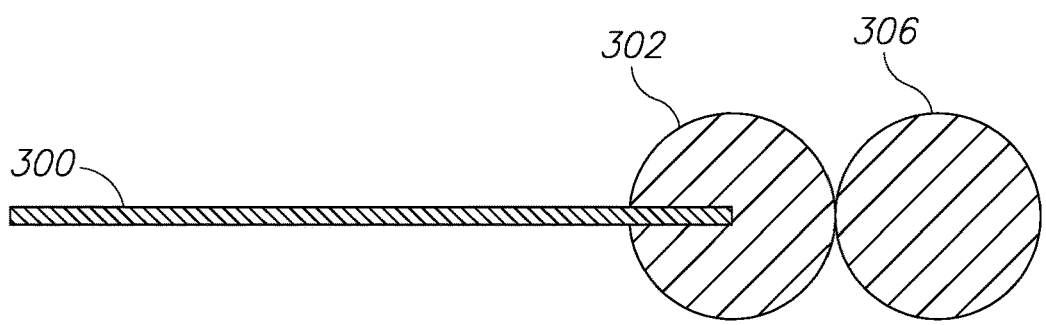
Figure 3C:
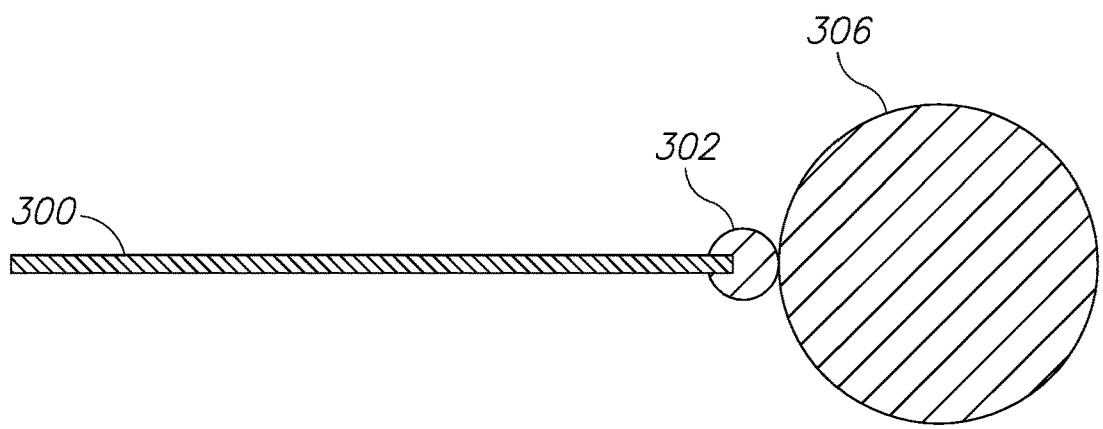

In order to achieve the above objectives as shown in FIG. 2, the following discussion may be a desirable procedure. As may be seen in FIG. 3A, a first laser pulse is initiated through fiber 300 to create a small bubble 302 around the tip 304 of the fiber 300. After a time delay, a second laser pulse is initiated to create a second bubble 306 which forms distally of the first bubble 302, as seen in FIG. 3B. Next, as the first bubble 302 collapses, the second bubble 306 grows in dimensions. A larger, second-distal bubble which is larger than the first-proximal bubble is a preferred result to push away from the tip of the scope and the fiber the damaging cavitation forces. As can be seen in FIG. 3C, that bubble 306 does not touch or be centered around the fiber tip 304 or the endoscope tip for that matter.

Figure 3D:
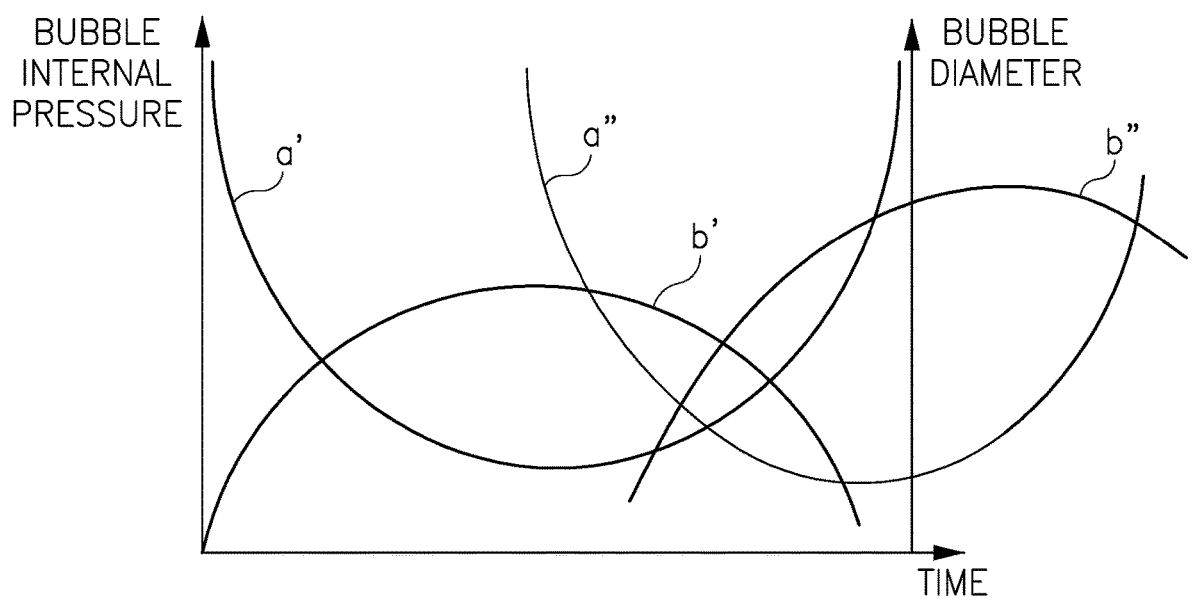
FIG. 3D is a graphical representation of bubble formation in the present invention.

Referring now to FIG. 3D, there is shown a typical bubble dynamic over time. The pressure inside a developed bubble is qualitatively represented by line a' and the bubble diameter is qualitatively represented by line b'. It can be seen that at the initiation of the bubble there is a high pressure inside the bubble which is reduced as the diameter of the bubble grows. At some point of equilibrium with the surrounding ambient pressure, the bubble stops its growth and the vapor inside starts to cool down. This eventually leads to the opposite dynamic in which the diameter starts to decrease, and the internal pressure starts to grow again. This process ends as a cavitation. Since by nature, the first bubble is centralized around the tip of the fiber and since by nature the bigger the bubble the stronger the cavitation energy, it is one aspect of the invention to initiate a first, smaller, bubble and a second, bigger, "main" bubble. The pressure inside the second formed bubble is qualitatively represented by line a", and the bubble diameter is qualitatively represented by line b". Therefore, according to an aspect of the present invention, a first bubble is created, and a second bubble is created in a certain time delay, in a certain time window thereafter, so that the increased pressure of the first bubble during its collapse will promote the inflation of the second bubble.

While the above discussion and the figures describe two pulses, it is to be understood that the regime may be three pulses in seriatim. The first and second pulses may be utilized to form and maintain the bubble and the third pulse utilized as a treatment pulse. However, the present invention is not restricted to three pulses but could be any number as dictated by such factors as the type of treatment, the energy of the respective pulses, the liquid environment, the distance from the fiber tip to the target tissue, etc.

Thus, as can be seen, by manipulating bubble formation techniques, degradation of the fiber tip and the distal tip of the endoscope is reduced while creating bubbles that increase the efficiency of the laser interaction with the target tissue—photo-mechanically for tissue separation or photo-thermally for tissue ablation or coagulation.

Interleaving of Laser Pulse Repetition Rates

Figure 4A:
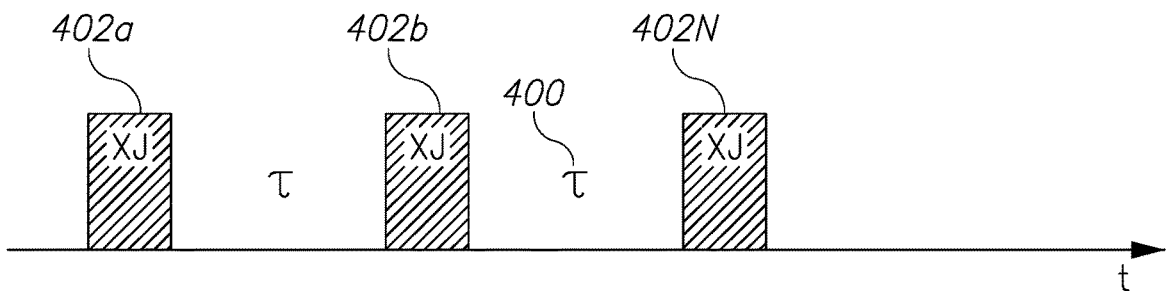
FIGS. 4A through 4C illustrate timing aspects of pulse formation in the present invention.

In a current MOSES™ system as implemented by the assignee of the present invention, the laser may fire a train of laser pulses, which may use identical settings for each pulse, and may use a constant repetition rate, as seen in FIG. 4A, in which the symbol T at 400 represents the time period between successive pairs of pulses 402a, 402b, 402n. Thus, under these foregoing parameters, a train of identical pulses is generated, equally spaced in time. Each pulse thus may be initiated using the same energy setting, the same peak power (or pulse duration), and if MOSES™ mode is used, the same MOSES™ mode parameters.

Figure 4B:
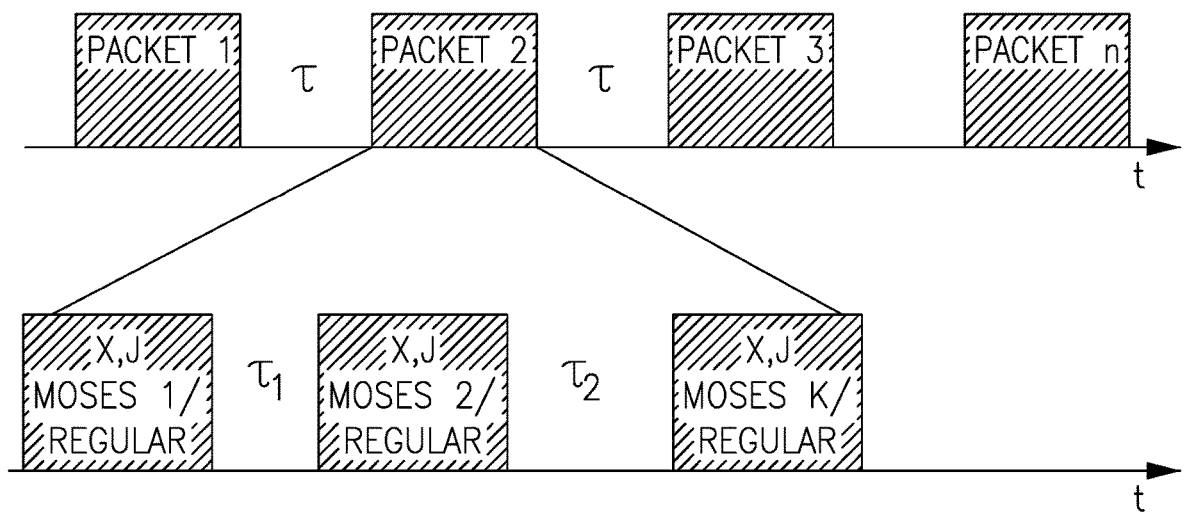

However, rather than implementing using identically-timed pulses, as in FIG. 4A, a pulse regime may be created to generate a periodic train of pulses packet, in which each pulse in the packet may have different parameters, and the spacing of the pulses within the packet can be varied as well, as illustrated graphically in FIG. 4B. Each pulse designated as pulse MOSES™ 1, 2, k shown in FIG. 4B may vary from other ones by the number of sub-pulses (as mentioned typically MOSES™ is implemented in a two sub-pulse regime), total energy, energy distribution between sub-pulses, as well as time intervals between sub-pulses.

The interleaving described in connection with FIG. 4B enables optimized combination of properties of different pulse modes, to achieve an improved tissue effect, relative to what is possible with a non-interleaved progression of identical pulses, such as tissue mechanical separation, tissue thermal ablation or tissue thermal coagulation.

Figure 4C:
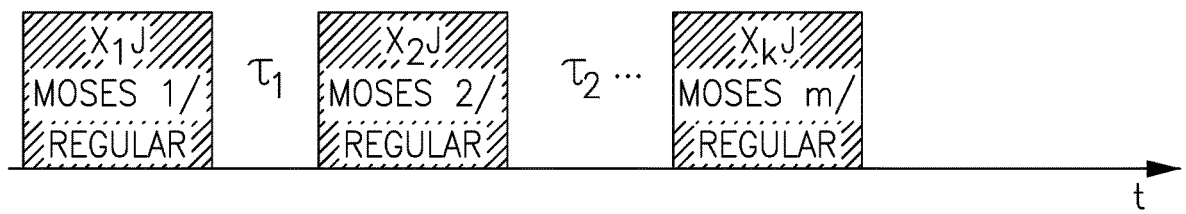

Further, as shown in FIG. 4C, it may be useful to provide a non-periodic laser activation process in which each pulse may have its unique parameters, and the spacing of the pulses can be varied as well. This variability may be useful depending on the type of treatment desired. MOSES™ pulses may be used to optimize the amount of optical energy delivered to a target tissue or the liquid medium for the purpose of ablation, coagulation or creating an optical-mechanical effect in a target tissue. A train of pulses may consist of a first one or more sub-pulses, which are configured to generate a first bubble centered on tip of an optical fiber and may be followed by a second one or more sub-pulses, which are configured to generate a second bubble. The first bubble spaces the second bubble so that the center of the second bubble is longitudinally displaced from the tip of the optical fiber. The collapse of the second bubble, therefore, reduces the burnback of the fiber and may increase the mechanical separation of a target tissue. The one or more first pulses may be generated with a laser having a first wavelength and the one of more second pulses may be generated by a laser having a second wavelength. According to one embodiment, the first laser wavelength and the second laser wavelength are the same and may be generated by the same type of laser such as for example Holmium, Thulium or Erbium. According to another embodiment, the first laser wavelength and the second laser wavelength are different. For example, the first laser wavelength may be a Thulium laser wavelength and the second laser wavelength may be a Holmium laser wavelength.

For example, some possible uses of this technique may include:

1. Stone lithotripsy—popcorn mode. In this mode the convection of the fluids is used to bring stones in front of the fiber, which are then broken by laser pulses. The convection is caused by laser pulses, which in this case should have a large bubble. The stone breaking is best done by MOSES™ mode pulses, e.g. low energy high repetition rate "dusting mode" settings, which do not cause sufficient convection. Interleaving pulses optimized to cause cavitation with pulses optimized for stone dusting can significantly improve pop-corning, or pop-dusting procedures.

2. Prostate enucleation—improved tissue separation. In this mode several pulses can be placed close together within the packet. Some of the pulses can be optimized to provide best mechanical tissue separation (photo-mechanical effect), while the following pulses can be optimized for best tissue cutting (photo-thermal effect). In this way the first pulses "stretch" the tissue, preparing it for the following pulses, which do the incision more effectively.

3. Prostate enucleation or ablation—improves hemostasis. This combination can be used for treating vascular prostates. Some pulses of the packet will be optimized for best tissue treatment (incision or ablation), while the following will be optimized for best coagulative properties.

4. Stones treatment—dynamic changes in the pulse optimization, such as (contact/distance/fragmentation/dusting).

A Bubble Shaping Element

Heretofore, there has been described a number of techniques to control and customize bubble(s) formation suited for one purpose or another. These have been achieved largely by non-physical modifications involving manipulation of, for example, timing of laser initiations, etc. However, physical modifications to the laser apparatus, and in particular to the distal portion of the endo scope, may result in the ability to manipulate bubble shapes, size, etc.

Turning now to FIGS. 5A through 5D, illustrated are various type of "chokes" that may be attached to the distal end of an endoscope or to the distal end of the fiber itself. A bubble shaping element may be configured to shape one or more bubbles created at the tip of an optical fiber during laser treatment in a liquid environment. Bubble shaping elements, such as bubble shaping elements 502, 510, 512 and 514, may be mounted or attached to the distal portion of the endoscope 500 or the fiber 508 and has a proximal end 504 which is configured to be connected or engaged with an area adjacent a distal end of an optical fiber 508 or the distal end of the endoscope 500. A distal end of the fiber shaping element is configured to allow fluid communication between an inner cavity in the bubble shaping element and the treatment surroundings.

During laser treatment, a bubble which is developed at the distal end of the optical fiber is restricted to expand in certain dimensions and free to expand in others. According to the embodiments of the present invention illustrated in FIGS. 5A through 5D, the bubble shaping elements 502, 510, 512 and 514 restrict one or more bubbles from expanding along an axis which is approximately perpendicular to the longitudinal axis 516 of the optical fiber and allows a bubble 600 to grow along the longitudinal axis 516 of the optical fiber.

The bubble shaping element may have a diverging shape (502), a converging shape (510), a straight shape (512), have a narrow cross-section (514), or be in a frustoconical shape or other shapes in order to control the bubble dimensions and formation.

The bubble shaping elements shown in FIGS. 5A through 5D allow a bubble 600 to grow more along an axis which connects the distal end of an optical fiber and a target tissue and restricts the growth of the bubble 600 along an axis approximately perpendicular to this axis. Since the gas bubble in a liquid environment is a more effective channel to deliver optical energy to a target tissue due to its lower absorption than the surrounding liquid environment, the bubble shaping element allows improving the ratio between the amount of energy needed to create a bubble and the longitudinal size of the bubble. In this case, optimization means that the less energy is "wasted" to develop a bubble and to grow the bubble until it reaches a target tissue in order to create the required MOSES™ or other desired effect; more energy is then available to be delivered through the bubble into the target tissue in order to get the desired treatment effects.

Figure 5A:
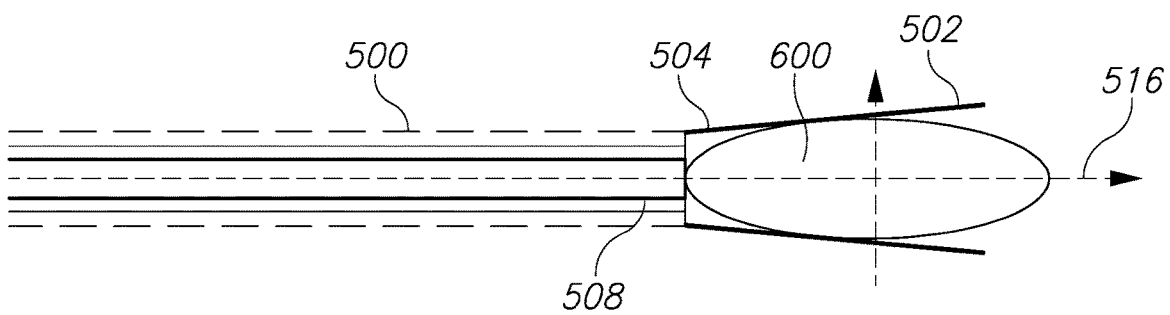
FIGS. 5A though 5D illustrate various chokes which may be utilized at the distal ends of either an optical fiber or an endoscope.
Figure 5B:
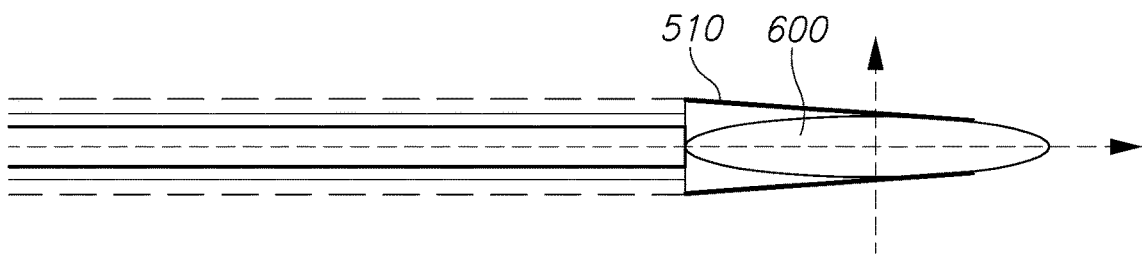
Figure 5C:
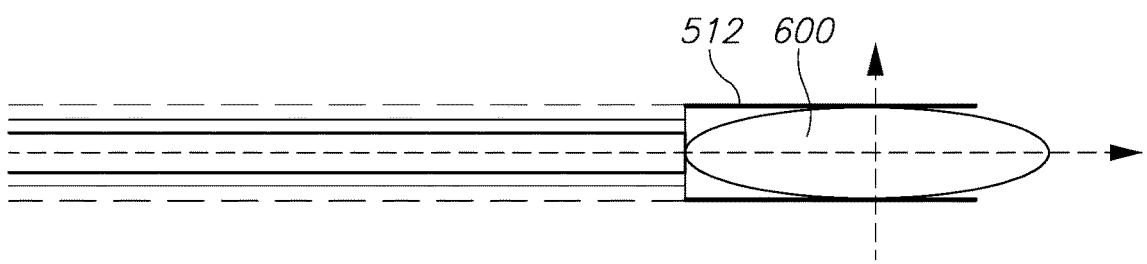
Figure 5D:
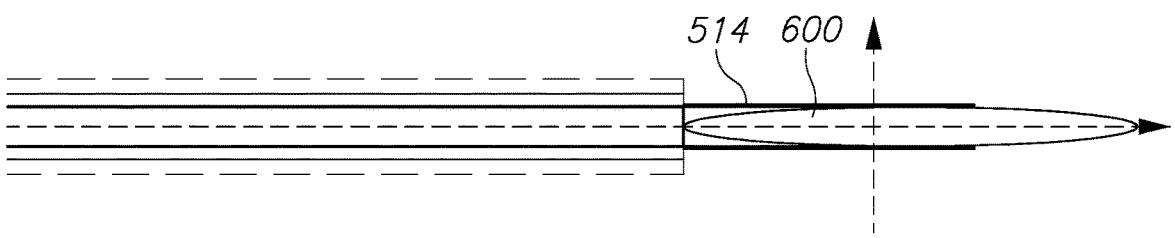

While 4 different types chokes are illustrated in FIGS. 5A though 5D, it is submitted that many other varieties are feasible. In addition, an adjustable choke may be implemented, much the same as the adjustable chokes employed on shotguns, by which a mechanism is adjusted to change the shape of the choke to suit particular treatment parameters.

What we claim is:

1. A method of treating a target tissue with a laser beam, said target tissue being immersed in a liquid medium within a body lumen, the method comprising:
providing a laser device for generating a laser beam;
providing an endoscope configured to be introduced into the body lumen, the endoscope having a distal end portion;
providing an optical fiber configured to be contained in the endoscope and having a distal delivery end for guiding the laser beam to the target tissue, wherein the distal delivery end protrudes a distance from the distal end portion of the endoscope;
providing a controller for causing the laser device to generate one or more laser pulses substantially along a longitudinal axis defined by the optical fiber delivery end;
the controller causing the laser device to provide one or more laser pulses, the one or more laser pulses being configured by the controller to have an energy sufficient to form one or more vapor bubbles in the liquid medium at the distal delivery end of the fiber;
the one or more pulses being selected by the controller:
first, causing a vapor bubble to be formed distally of the distal end portion of the endoscope and around the distal delivery end of the optical fiber;
second, causing a second vapor bubble to be formed distally of the first bubble, the second vapor bubble being distal of both the endoscope distal end portion and the optical fiber distal delivery end;
third, inflating the second bubble as the first bubble has begun to collapse to expand an amount sufficient to displace a substantial portion of the liquid medium from the space between the distal delivery end of the fiber and the target tissue, the one or more pulses being delivered to the target tissue through the inflated second bubble; and,
wherein the displacement of the second bubble away from the distal portion of the endoscope and the distal delivery end of the optical fiber reduces wear and/or injury to one or more of the endoscope and the optical fiber.

2. The method of claim 1, wherein the one or more laser pulses is more than one train of pulses, further comprising the step of the controller of selecting a repetition rate for delivery of the more than one laser pulses.

3. The method of claim 1, further comprising:
selecting at least the following parameters through the controller: selecting the total energy of one or more pulses to be delivered to the target tissue, and selecting the distance from the delivery end to the target tissue.

4. The method of claim 3, further comprising the steps of: measuring actual energy irradiated by the laser device; comparing the actual measured energy to a total energy selected by the controller; and, if the comparison demonstrates variance of the actual measured energy from the selected total energy, the controller adjusting the energy for any following pulses to achieve the selected energy delivered to the target tissue.

5. The method of claim 4, wherein the step of measuring the actual energy delivered by the laser is performed by a photodetector in the light path of the laser radiation.

6. The method of claim 4, wherein the step of the controller adjusting the energy is accomplished by a closed loop feedback circuit operatively connected to the controller.

7. The method of claim 3, wherein the step of selecting the distance from the delivery end to the target tissue includes the further step of measuring the distance and selecting the measured distance.

8. The method of claim 1, wherein the target tissue is a tissue, an organ or a formed stone within a human body.

9. The method of claim 1, further comprising the step of selecting and mounting on the laser device an optical fiber type to be used in irradiating the target tissue.

10. The method of claim 9, wherein the type of optical fiber includes at least one of the parameters of: fiber diameter, fiber material, fiber numerical aperture and shape of the distal delivery end.

11. The method of claim 10, wherein the controller intermittently recognizes parameters associated with the fiber type mounted on the laser device.

12. The method of claim 10, wherein the step of automatically recognizing is performed by a RFID identification tag mounted on the delivery device and on the waveguide or optical fiber.

13. The method of claim 10, wherein the controller indicates on a user interface associated with the controller if the optical fiber type is compatible with a treatment selected.

14. Apparatus for the treatment of a target tissue with a laser beam, said target tissue being immersed in a liquid medium within a body lumen, the apparatus comprising:
a laser device for generating a laser beam;
an endoscope configured to be introduced into the body lumen, the endoscope having a distal end portion;
an optical fiber configured to be contained in the endoscope and having a distal delivery end for guiding the laser beam to the target tissue, wherein the distal delivery end protrudes a distance from the distal end portion of the endoscope;
a controller for causing the laser device to generate one or more laser pulses substantially along a longitudinal axis defined by the optical fiber delivery end;
wherein the laser device is configured to provide one or more laser pulses, the one or more laser pulses being configured by the controller to have an energy sufficient to form one or more vapor bubbles in the liquid medium at the distal delivery end of the fiber;
the one or more pulses being configured by the controller to:
first, cause a vapor bubble to be formed distally of the distal end portion of the endoscope and around the distal delivery end of the optical fiber;
second, cause a second vapor bubble to be formed distally of the first bubble, the second vapor bubble being distal of both the endoscope distal end portion and the optical fiber distal delivery end;
third, inflate the second bubble as the first bubble has begun to collapse to expand an amount sufficient to displace a substantial portion of the liquid medium from the space between the distal delivery end of the fiber and the target tissue, the one or more pulses being delivered to the target tissue through the inflated second bubble; and,
wherein the displacement of the second bubble away from the distal portion of the endoscope and the distal delivery end of the optical fiber reduces wear and/or injury to one or more of the endoscope and the optical fiber.

* * * * *